US00PP15715P2

(12) United States Plant Patent
Jennings et al.

(10) Patent No.: US PP15,715 P2
(45) Date of Patent: Apr. 12, 2005

(54) ***EUPHORBIA* PLANT NAMED 'TASMANIAN TIGER'**

(50) Latin Name: *Euphorbia characias*
Varietal Denomination: Tasmanian Tiger

(76) Inventors: Barbara Jennings, 11 Morgan Street, Hobart, Tas (AU); Sally Johannsohn, 1115 Hoon Road, Neika, Tas. (AU), 7054

( * ) Notice: Subject to any disclaimer, the term of this patent is extended or adjusted under 35 U.S.C. 154(b) by 0 days.

(21) Appl. No.: 10/678,449

(22) Filed: Oct. 6, 2003

(30) Foreign Application Priority Data

Apr. 23, 2001 (QZ) ..... PBR 20019999

(51) Int. Cl.[7] ..... A01H 5/00

(52) U.S. Cl. ..... Plt./302

(58) Field of Search ..... Plt./302

*Primary Examiner*—Kent Bell

(57) ABSTRACT

A new cultivar of *Euphorbia* named 'Tasmanian Tiger' that is distinguished by a compact habit, tall inflorescences with cream-white flowers, white and grey-green variegated foliage, and pale grey-green stems. In combination these traits set 'Tasmanian Tiger' apart from all other existing varieties of *Euphorbia* known to the inventor.

2 Drawing Sheets

Genus: *Euphorbia.*
Species: *characias.*
Denomination: Tasmanian Tiger.

BACKGROUND OF THE INVENTION

The present invention relates to a new and distinct cultivar of spurge, a hardy perennial, that is grown for use as an ornamental landscape plant. The new invention is known botanically as *Euphorbia characias* and will be referred to hereinafter by the cultivar name 'Tasmanian Tiger'.

In 1993 'Tasmanian Tiger' was discovered and selected by the inventor, in a cultivated area of Tasmania, Australia. 'Tasmanian Tiger' is a chance hybrid plant that resulted from the open pollination between the parent plants. 'Tasmanian Tiger' grew from seed that was collected from *Euphorbia characias* subsp.*wulfenii* 'Lambrook Gold'. The female or seed parent plant is *Euphorbia characias* subsp. *wulfenii* 'Lambrook Gold' (unpatented) and the male or pollen parent is an unidentified cultivar of *Euphorbia characias.* 'Tasmanian Tiger' is distinguishable from the female parent plant by variegated grey-green and white foliage, and cream-colored flowers. The female parent plant exhibited variation in leaf color, exhibited low vigor, and subsequently died. The leaf color of 'Tasmanian Tiger' is uniform and consistent, and the plant exhibits a vigorous growth habit.

'Tasmanian Tiger' is an ornamental plant selected for its variegated leaves that exhibit grey-green centers and white margins, compact rounded growth habit, pale grey-green stems and tall flower spikes covered with cream-white flowers. There are no comparison plants known to the inventor.

The first asexual reproduction of 'Tasmanian Tiger' was conducted in 1994 by the inventor in Tasmania, Australia. The method used was softwood cuttings. Since that time subsequent generations have been determined stable and true to type. 'Tasmanian Tiger' can also be propagated using the method of tissue culture.

SUMMARY OF THE INVENTION

The following traits have been repeatedly observed and represent the distinguishing characteristics of the new *Euphorbia* cultivar 'Tasmanian Tiger'. These traits in combination distinguish 'Tasmanian Tiger' from all other existing varieties of *Euphorbia* known to the inventor. 'Tasmanian Tiger' has not been tested under all possible conditions and phenotypic differences may be observed with variations in environmental, climatic, and cultural conditions, however, without any variance in genotype.

1. *Euphorbia* 'Tasmanian Tiger' exhibits a compact, rounded growth habit.
2. *Euphorbia* 'Tasmanian Tiger' exhibits a profusion of cream-white flowers in spring and summer.
3. *Euphorbia* 'Tasmanian Tiger' exhibits variegated leaves with grey-green centers and white margins.
4. *Euphorbia* 'Tasmanian Tiger' exhibits pale grey-green stems.
5. *Euphorbia* 'Tasmanian Tiger' is propagated using the methods of soft stem cuttings or tissue culture.
6. *Euphorbia* 'Tasmanian Tiger' exhibits large inflorescences on tall flower spikes.
7. *Euphorbia* 'Tasmanian Tiger' is 1 meter in height and 1 meter in width at maturity.

BRIEF DESCRIPTION OF THE DRAWING

The accompanying color drawing illustrates the overall appearance of the new *Euphorbia* cultivar 'Tasmanian Tiger' showing the colors as true as it is reasonably possible to obtain in colored reproductions of this type. Colors in the photograph may differ from the color values cited in the detailed botanical description, which accurately describe the actual colors of the new variety 'Tasmanian Tiger'.

The drawing on sheet 1 illustrates the entire plant in bloom from a side perspective.

The drawing on sheet 2 illustrates a close-up view of the inflorescence. Both drawings were made using conventional techniques and although flower and foliage colors may appear different from actual colors due to light reflectance, they are as accurate as possible by conventional photography.

BOTANICAL DESCRIPTION OF THE PLANT

The following is a detailed botanical description of the new *Euphorbia* cultivar 'Tasmanian Tiger'. Observations, measurements, values and comparisons were collected in Arroyo Grande, Calif. from 2-liter container plants that were 18-months-old and grown out-of-doors in full sun. Color determinations are made in accordance with The 2001 Royal Horticultural Society Colour Chart from London England, except where general color terms of ordinary dictionary significance are used. The growing requirements of the new variety are similar to the species and there are no known growing problems, diseases or pests.

Botanical classification: *Euphorbia* 'Tasmanian Tiger'.
Species: *characias*.
Common name: Spurge.
Commercial classification: Shrub.
Parentage: *Euphorbia* 'Tasmanian Tiger' is a chance hybrid plant that resulted from the open pollination between the following parent plants:
- *Female parent.*—*Euphorbia characias* subsp. *wulfenii* 'Lambrook Gold'.
- *Male parent.*—An unidentified cultivar of *Euphorbia characias*.

Propagation method: Softwood cuttings and tissue culture.
Rooting habit: Fibrous.
Time to develop roots: 8 weeks are needed on bottom heat for roots to develop on an initial cuttings.
Temperature recommended to develop roots: 10°–20° Centigrade.
Crop time: 9 months are needed to produce a finished 1-liter container from a rooted cutting.
Growth habit: Compact habit with tall flowering spikes from central crown.
Shape: Well-rounded shape.
Use: Ornamental plant for the landscape.
Type: Perennial herb.
Vigor: Vigorous.
Height of plant: 1 meter in height at maturity and 20 cm. in height in a 2-liter container.
Width of plant: 1 meter in width at maturity and 22 cm. in width in a 2-liter container.
Cultural requirements: Full sun and well-draining soil.
Diseases and pests: None known to the inventor.
Hardiness: Hardy to minus 8° Centigrade.
Special growing requirements: None known to the inventor.
Special considerations: All parts exude a white milky substance when bruised that can be toxic and may elicit dermal irritation.

Stem:
- *Branching habit.*—Central stem.
- *Stem color.*—193A.
- *Stem shape.*—Cylindrical to columnar.
- *Stem width.*—1 cm. in width.
- *Stem length.*—17 cm. in length.
- *Stem surface.*—Pubescent.

Foliage:
- *Type.*—Evergreen.
- *Leaf arrangement.*—Whorled.
- *Leaf division.*—Simple.
- *Leaf shape.*—Linear to ensiform.
- *Leaf length.*—9 cm. in length.
- *Leaf width.*—0.75 cm. in width.
- *Leaf apex.*—Acuminate.
- *Leaf base.*—Truncate.
- *Quantity of leaves.*—Approximately 100 per stem on basal half.
- *Leaf venation pattern.*—Parallel with a prominent mid vein.
- *Vein color* (*abaxial surface*).—191C.
- *Vein color* (*adaxial surface*).—158D.
- *Margin.*—Entire and pubescent.
- *Leaf surface* (*abaxial surface*).—Pubescent.
- *Leaf surface* (*adaxial surface*).—Pubescent.
- *Leaf appearance* (*adaxial and abaxial surfaces*).—Dull.
- *Leaf attachment.*—Sessile.
- *Leaf color* (*center and margins of adaxial surface*).—Center is 191A and margin is 158D.
- *Leaf color* (*center and margins of abaxial surface*).—Center is 191C and margin is 158D.
- *Internode dimensions.*—0.25 cm. between nodes.

Flower:
- *Type.*—Inflorescence.
- *Dimensions of individual cyathium.*—3 cm. in diameter and 5 cm. in length.
- *Quantity of flowers per cyathium.*—7 flowers per cyathium.
- *Type of inflorescence.*—Cyathium.
- *Flowering season.*—Spring and summer.
- *Flower aspect.*—Facing upward and outward.
- *Peduncle dimensions.*—The dimensions of peduncle range from 5–10 cm. in length and are 0.75 cm. in width.
- *Peduncle color.*—193A.
- *Peduncle shape.*—Cylindrical.
- *Peduncle surface.*—Puberulent.
- *Number of cyathium per peduncle.*—The average number is 147 cyathium per peduncle.
- *Pedicel dimensions.*—Pedicels range from 1.50–2 cm. in length and from 2–3 mm. in width.
- *Pedicel color.*—193A.
- *Pedicel shape.*—Cylindrical.
- *Pedicel surface.*—Pubescent.
- *Petals.*—Apetalous.
- *Sepals.*—Asepalous.
- *Bract attachment.*—Connate perfoliate.
- *Dimensions of bract.*—12 mm. in length and 1.75 cm. in width.
- *Shape of bract.*—Closest to deltoid but with obuse apex.
- *Color of bract* (*adaxial and abaxial surfaces*).—155B and 191A (small amount) are both individually present on both surfaces of an individual bract.
- *Number of bracts per cyathium.*—Fourteen bracts in number per cyathium.
- *Number of bracts per involucre.*—Two bracts in number per involucre.
- *Shape of involucre.*—Cupulate to funnel-shaped.
- *Bracts fused or unfused.*—The two bracts per involucre are fused.
- *Number of involucres per cyathium.*—Seven involucres in number per cyathium.
- *Bract margins.*—Entire.
- *Margins of cyathium.*—Entire.

*Color of cyathia.*—155B and 191A (small amount) are both individually present on an individual cyathium.
*Flower fragrance.*—None observed.
*Bud shape.*—Oval to globose.
*Bud dimensions.*—3 mm. in diameter and 5 mm. in length.
*Bud color.*—4D.

Reproductive organs:
*Stamen color.*—155A.
*Stamen dimensions.*—Less than 0.50 mm. in length and 1 mm. in diameter.
*Anther shape.*—Horseshoe.
*Anther color.*—162A.
*Anther dimensions.*—Less than 0.50 mm. in width and less than 0.50 mm. in length.
*Pollen.*—Present.
*Quantity of pollen.*—Moderate amount.
*Pollen color.*—11A.
*Ovary.*—None observed to date.
*Color of pistil.*—155A.
*Surface of individual pistil.*—Lanate surface.
*Shape of pistil.*—Globular.
*Number of pistils.*—Four pistils per individual cyathium.
*Style color.*—155A.
*Stigma color.*—11D.
*Dimensions of stigma.*—Less than 1 mm. in length and less than 0.50 mm. in width.
*Stigma shape.*—Branched with six small branches.

Seed: No seed has been observed to date.

What is claimed is:

1. A new and distinct cultivar of *Euphorbia* plant named 'Tasmanian Tiger' as described and illustrated.

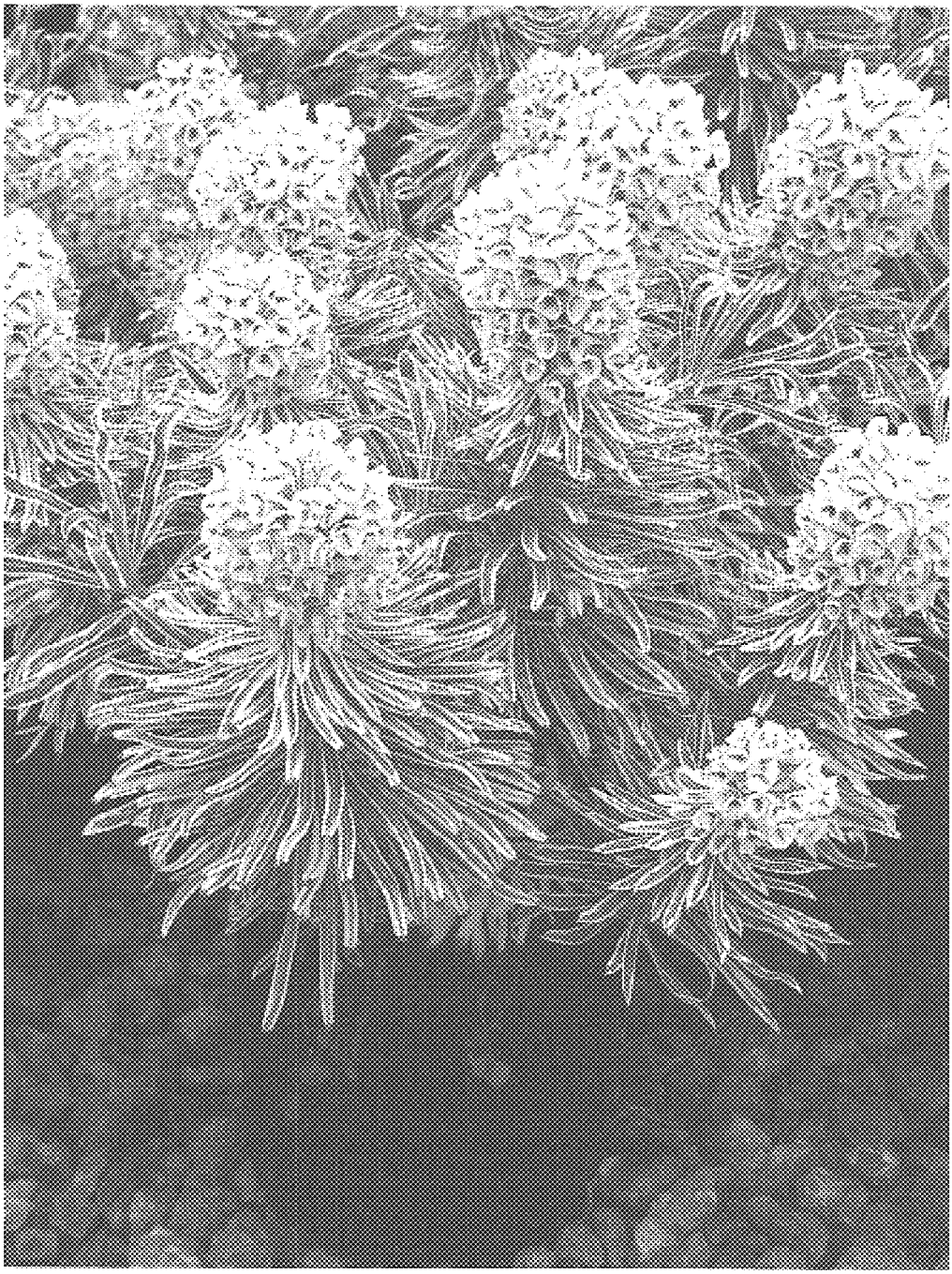

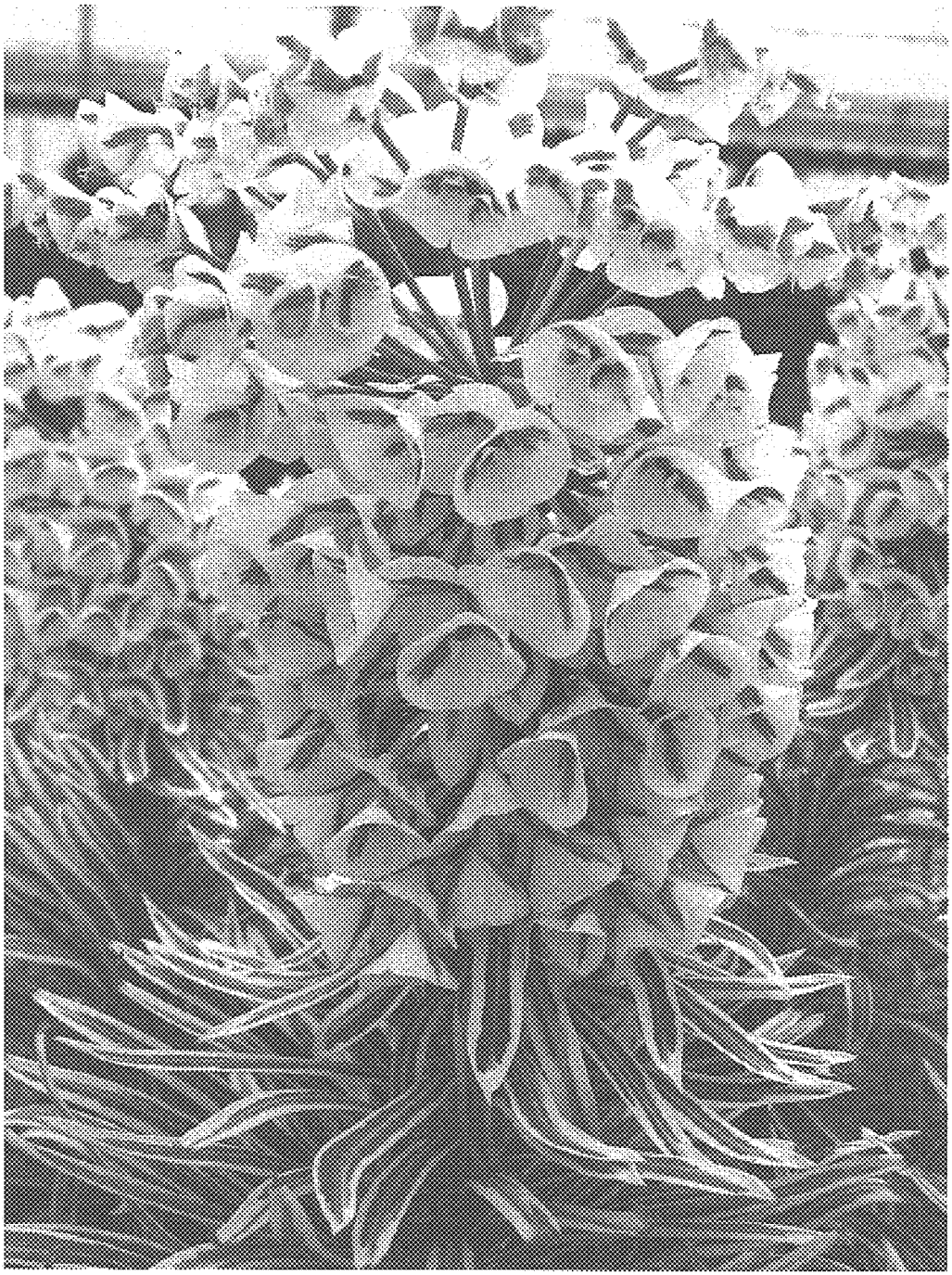

* * * * *